United States Patent [19]

Sacrini et al.

[11] 3,980,712

[45] Sept. 14, 1976

[54] ORGANIC PEROXIDES THEIR PREPARATION AND THEIR APPLICATIONS

[75] Inventors: Egeo Sacrini; Claudio Cavallotti, both of Milan, Italy

[73] Assignee: The B. F. Goodrich Company, Akron, Ohio

[22] Filed: June 26, 1973

[21] Appl. No.: 374,009

Related U.S. Application Data

[62] Division of Ser. No. 62,128, Aug. 8, 1970, Pat. No. 3,775,465.

[30] Foreign Application Priority Data

Aug. 12, 1969   Italy.................................. 20839/69

[52] U.S. Cl............................................ 260/610 R
[51] Int. Cl.²...................................... C07C 179/00
[58] Field of Search........ 260/610 A, 610 R, 610 B, 260/485 R, 88.2 R, 485 R

[56] References Cited

UNITED STATES PATENTS

| | | | |
|---|---|---|---|
| 2,455,569 | 12/1948 | Dickey............................ | 260/610 R |
| 2,537,853 | 1/1951 | Pezzagelia...................... | 260/610 R |
| 2,715,646 | 8/1955 | Hawkins et al.................. | 260/610 B |
| 3,190,924 | 6/1965 | Sodomann et al. ............. | 260/610 B |
| 3,775,465 | 1/1973 | Sacrina et al................ | 260/475 S C |

FOREIGN PATENTS OR APPLICATIONS 1,058,950   2/1967   United Kingdom............ 260/610 R Primary Examiner—James O. Thomas, Jr.
Assistant Examiner—W. B. Lone
Attorney, Agent, or Firm—Hubbell, Cohen, Stiefel & Gross

[57] ABSTRACT

Tetraperoxides of the formula

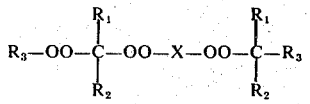

where X is a bivalent radical such as alkylene; $R_1$ is hydrogen or an organic radical; $R_2$ is alkylene alkoxy carbonyl; and $R_3$ is an organic radical. Method of preparing tetraperoxides by addition reaction between a bis-hydroperoxide and a carbonyl compound to form a dihydroxy diperoxide, followed by condensation of the dihydroxy diperoxide with a tertiary monohydroxide. The tetraperoxides are useful for vulcanizing saturated elastomers, crosslinking plastomers, and initiating radical polymerization.

8 Claims, No Drawings

ORGANIC PEROXIDES THEIR PREPARATION AND THEIR APPLICATIONS

This is a division of application Ser. No. 62,128, filed Aug. 8, 1970 now U.S. Pat. No. 3,775,465.

BACKGROUND OF THE INVENTION

1. Field of the Invention

The present invention relates to a new series of organic peroxides. More particularly, it relates to a process for the preparation of peroxides having four peroxidic functions, to novel peroxides having four peroxidic functions, and to the use of such peroxides as radical polymerization initiators, vulcanizing agents for elastomers, crosslinking agents for plastomers, and as organic reactants.

2. Description of the Prior Art

It is well known that organic compounds of a peroxidic nature are important as generators of free radicals and consequently as initiators of free radical polymerizations, as crosslinking agents for plastomers and as vulcanizing agents for elastomers.

THE INVENTION

The present invention provides a particular type of new organic peroxides having good stability and low volatility at temperatures higher than room temperature, such peroxides being particularly suitable both as vulcanizers for elastomers and as crosslinking agents for plastomers.

The present invention provides a new series of organic peroxides characterized by the presence of four peroxidic groups, these peroxides being defined by the general formula:

$$R_3-OO-\underset{\underset{R_2}{|}}{\overset{\overset{R_1}{|}}{C}}-OO-X-OO-\underset{\underset{R_2}{|}}{\overset{\overset{R_1}{|}}{C}}-OO-R_3$$

wherein: each of $R_1$ may be hydrogen, alkyl, haloalkyl, cycloalkyl, halocycloalkyl, alkylcycloalkyl, said groups having 1–15 C, aryl, haloaryl, alkaryl, said groups having 6–15 C, oxyalkyl, oxyalkylaryl, or oxycycloalkyl, said groups having 1–15 C; each of $R_2$ may be alkylene alkoxy carbonyl wherein alkylene group has 1–4 C and alkoxy group has 1 to 4 C such as methylene ethoxy carbonyl,

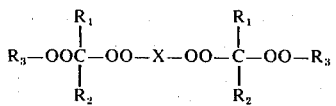

or the like; each of $R_3$ may be alkyl, haloalkyl, said groups having 4–12 C, cycloalkyl, halocycloalkyl, alkylcycloalkyl, said groups having 4–21 C, aryl, alkaryl, haloaryl, said groups having 6–24 C, oxyalkyl, oxyalkylaryl, oxycycloalkyl, said groups having 4–24 C, or acyl, having 6–12 C; preferred radicals being tertiary alkyl such as tert.-butyl, tert.-amyl, and cumyl; and X is alkylene, haloalkylene, arylalkylene, said groups having 2–18 C, alkenylene, halo-alkenylene, arylalkenylene, said groups having 2–18 C, alkinylene, haloalkinylene, aryl alkinylene, said groups having 2–18 C, oxyalkylene, having 2–12 C, arylene, alkyl arylene, or halo arylene, said groups having 6–18 C.

Examples of compounds within the above cited general formula include:
1. α-α' [2-tert.-butyl peroxy-(3-ethoxycarbonyl)-isopropylidene-2 peroxy] 1,3 diisopropylbenzene,
2. α-α' [2-tert.-butyl peroxy-(3-ethoxycarbonyl)-isopropylidene-2 peroxy] 1,4 diisopropylbenzene,
3. α-α' [2-cumyl peroxy-(3-ethoxycarbonyl)-isopropylidene-2 peroxy] 1,3 diisopropylbenzene,
4. α-α' [2-cumyl peroxy-(3-ethoxycarbonyl)-isopropylidene-2 peroxy] 1,4 diisopropylbenzene.

The peroxides of this invention show the unusual properties of being endowed with a good stability and a low volatility at temperatures higher than room temperature. These properties permit the compounds to be readily incorporated both into the plastomers as crosslinking agents, and into elastomers as vulcanizing agents, without giving rise to troublesome secondary phenomena.

This invention provides, moreover, a process for the preparation of the foregoing peroxides, as well as of other known tetraperoxides, e.g., those disclosed in U.S. Pat. No. 3,489,730 at column 1, lines 41–59, the contents of which are incorporated herein by reference, through two successive steps. In the first step there occurs an addition reaction between a bis-hydroperoxide and a carbonyl compound, with the formation of a diperoxide having a double hydroxy function. In the second step there occurs a condensation reaction between the previously obtained diperoxide and a mono-hydroxide of the tertiary type.

According to a preferred embodiment, the desired tetraperoxides are prepared in the presence of a suitable solvent by reacting in the first step (1) an organic carbonyl compound of the formula: $R_1-CO-R_2$, wherein each of $R_1$ and $R_2$ may be hydrogen, alkyl, haloalkyl, cycloalkyl, halocycloalkyl, alkylcycloalkyl, said groups having 1–15 C, aryl radicals, haloaryl, alkaryl, said groups having 6–15 C, oxyalkyl-, oxyalkylaryl-, oxycycloalkyl, said groups having 1–15 C; $R_2$ may also be an alkylene alkoxy carbonyl wherein alkylene has 1 to 4 C and alcoxy has 1 to 4 C; or $R_1$ and $R_2$ together with the central carbon atom form a cycloaliphatic ring, having 4–16 C, which ring may be alkyl-, halogen-, or hydroxy- substituted, having 1–8 C, with (2) a bis-hydroperoxide of the formula: HOO—X—OOH, in which X has the previously defined meaning, the reaction being carried out in the presence of a suitable dehydrating agent and an acid catalyst, at a temperature of from about −30° to +80°C, preferably from about −10°C to +50°C.

The compound thus obtained is a diperoxide of the formula:

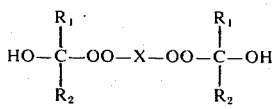

wherein $R_1$ and $R_2$ and X have the previously defined meanings.

Examples of compounds embraced by the above formula include:
a. α-α'(2-hydroxy-isopropylidene-2-peroxy) 1,3 diisopropylbenzene;
b. α-α' (2-hydroxy-isopropylidene-2-peroxy) 1,4 diisopropylbenzene;

c. α-α' (2-hydroxy-2-phenylethyl-2-idene-peroxy) 1,3 diisopropylbenzene;
d. α-α' [2-hydroxy-(3-ethoxycarbonyl)-isopropylidene-2-peroxy] 1,3 diisopropylbenzene;
e. α-α' [2-hydroxy-(3-ethoxycarbonyl)-isopropylidene-2-peroxy] 1,4 diisopropylbenzene;
f. α-α' (1-hydroxy-cyclopentylidene-1-peroxy) 1,3 diisopropylbenzene;
g. α-α' (1-hydroxy-cyclopentylidene-1-peroxy) 1,4 diisopropylbenzene;
h. α-α' (1-hydroxy-cyclohexylidene-1-peroxy) 1,3 diisopropylbenzene;
i. α-α' (1-hydroxy-cyclohexylidene-1-peroxy) 1,4 diisopropylbenzene;
j. α-α' (1-hydroxy-4-tert.-butyl-cyclohexylidene-1-peroxy) 1,3 diisopropylbenzene;
k. α-α' (1-hydroxy-4-tert.-butyl-cyclohexylidene-1-peroxy) 1,4 diisopropylbenzene;
l. α-α' (1-hydroxy-cyclododecylidene-1-peroxy) 1,3 diisopropylbenzene;
m. α-α' (1-hydroxy-cyclododecylidene-1-peroxy) 1,4 diisopropylbenzene;
n. α-α' (2-hydroxy-n-butyliden-2-peroxy) 1,3 diisopropylbenzene;
o. α-α' (4-hydroxy-2,6,8 trimethyl nonylidene-4-peroxy) 1,3 diisopropylbenzene;
p. α-α' [2-hydroxy-(3 phenyl)-propylidene-2-peroxy] 1,3 diisopropylbenzene.

The peroxides defined by the foregoing formula are new compounds, and are useful as initiators of radical polymerizations.

The diperoxides obtained as described above are then reacted in the second step of the process, with mono-hydroperoxides in the presence of suitable dehydrating agents and catalysts of an acid nature at a temperature between about −30° and +80°C, preferably between about −10° and +50°C.

Examples of bis-hydroperoxides which are suitable for use in the first step of the process include: diisopropylbenzene-1,3-dihydroperoxide; diisopropylbenzene-1,4-dihydroperoxide; 2,5-dimethyl-2,5-dihydroperoxyhexane; 2,5-dimethyl-2,5-dihydroperoxide-hexene-3; 2,5-dimethyl-2,5-dihydroperoxy-hexyne-3; etc.

Examples of carbonyl compounds suitable for use in the first step of the process include: aliphatic ketones such as methyl ethyl ketone, acetone; substituted aliphatic ketones such as ethyl-acetacetate; cyclo-ketones such as cyclopentanone, cyclohexanone and ccyclododecanone; cyclo-alkyl-ketones such as 4-terbutyl cyclohexanone; alkylarylaldehydes such as cinnamaldehyde; alkylheterocyclic aldehydes such as furyl acrylic aldehyde.

The mono-hydroperoxides which may be used in the second step of the process are the type: $R_3 - OOH$ wherein $R_3$ has the above defined meaning, preferably wherein a tertiary carbon atom is bound to the hydroperoxide group. Examples of such mono-hydroperoxides include: tert.-butyl hydroperoxide and substituted tert.-butyl hydroperoxides, cumyl hydroperoxide and substituted cumyl hydroperoxides, methyl-cyclohexyl hydroperoxide, 2-methyl-2 hydroperoxide-butyn-3, menthane hydroperoxide, etc.

Solvents suitable for use in this invention include linear aliphatic hydrocarbons having 6–10 C; linear aliphatic halogenated hydrocarbons having 1 or 2 C and 1 to 4 Cl; cycloaliphatic hydrocarbons having 6–10 C; aromatic hydrocarbons having 6–9 C, which may be halogenated with 1 or 2 Cl; ethers for instance, ethyl ether.

The molar ratio between the bis-hydroperoxide and the carbonyl compound used in the addition reaction should be between 1:1.2 and 1:10, and preferably between 1:1.5 and 1:5. Catalysts of an acid nature may be of the HCl, $H_2SO_4$ and $HClO_4$ type.

For the second step of the process, wherein a condensation reaction takes place, the molar ratio of diperoxide having a double hydroxy function to monohydroperoxide should be between 1:2 and 1:10, and preferably between 1:3 and 1:5.

As previously noted, the overall process of this invention can be employed to prepare a wide variety of tetraperoxides, many of which are known, many of which are new. Examples of tetraperoxides which can be made by the process of this invention include the following:

1. α-α' (2-cumyl peroxy-isopropylidene-2-peroxy) 1,3 diisopropylbenzene;
2. α-α' (2-cumyl peroxy-isopropylidene-2-peroxy) 1,4 diisopropylbenzene;
3. α-α' (2-tert.-butyl-peroxy-2-phenyl ethyl-2-idene-2-peroxy) 1,3 diisopropylbenzene;
4. α-α' (2-tert.-butyl-peroxy-2-phenyl ethyl-2-idene-2-peroxy) 1,4 diisopropylbenzene;
5. α-α' (2-cumyl peroxy-2-phenyl ethyl-2-idene-2-peroxy) 1,3 diisopropylbenzene;
6. α-α' (2-cumyl peroxy-2-phenyl ethyl-2-idene-2-peroxy) 1,4 diisopropylbenzene;
7. α-α' [2-tert.-butyl peroxy-(3-ethoxycarbonyl) isopropylidene-2-peroxy] 1,3 diisopropylbenzene;
8. α-α' [2-tert.-butyl peroxy-(3-ethoxycarbonyl) isopropylidene2-peroxy] 1,4 diisopropylbenzene;
9. α-α' [2-cumyl peroxy-(3-ethoxycarbonyl)-isopropylidene-2-peroxy] 1,3 diisopropylbenzene;
10. α-α' [2-cumyl peroxy(3-ethoxycarbonyl)-isopropylidene-2-peroxy] 1,4 diisopropylbenzene;
11. α-α' (1-tert.-butyl peroxy-cyclopentylidene-1-peroxy) 1,3 diisopropylbenzene;
12. α-α' (1-tert.-butyl peroxy-cyclopentylidene-1-peroxy) 1,4 diisopropylbenzene;
13. α-α' (1-cumyl peroxy-cyclopentylidene-1-peroxy) 1,3 diisopropylbenzene;
14. α-α' (1-cumyl peroxy-cyclopentylidene-1-peroxy) 1,4 diisopropylbenzene;
15. α-α' (1-tert.-butyl peroxy-cyclohexylidene-1-peroxy) 1,3 diisopropylbenzene;
16. α-α' (1-tert.-butyl peroxy-cyclohexylidene-1-peroxy) 1,4 diisopropylbenzene;
17. α-α' (1-cumyl peroxy-cyclohexylidene-1-peroxy) 1,3 diisopropylbenzene;
18. α-α' (1-cumyl peroxy-cyclohexylidene-1-peroxy) 1,4 diisopropylbenzene;
19. α-α' (1-tert.-butyl peroxy-4 tert.-butyl-cyclohexylidene-1-peroxy) 1,3 diisopropylbenzene;
20. α-α' (1-tert.-butyl peroxy-4 tert.-butyl-cyclohexylidene-1-peroxy) 1,4 diisopropylbenzene;
21. α-α' (1-tert.-butyl peroxy-cyclododecylidene-1-peroxy) 1,3 diisopropylbenzene;
22. α-α' (1-tert.-butyl peroxy-cyclododecylidene-1-peroxy) 1,4 diisopropylbenzene;
23. α-α' (2-tert.-butyl peroxy-n-butylidene-2-peroxy) 1,3 diisopropylbenzene;
24. α-α' (4-tert.-butyl peroxy-2,6,8 trimethyl nonylidene-4-peroxy) 1,3 diisopropylbenzene;
25. α-α' [2-tert.-butyl peroxy-(3 phenyl) propylidene-2-peroxy)] 1,3 diisopropylbenzene;

26. α-α′ [1-cumyl-peroxy-(4-tert.-butyl) cyclohexylidene-1-peroxy] 1,3 diisopropylbenzene.

Both the hydroxyl diperoxides and the tetraperoxides obtained according to this invention are soluble in aliphatic and aromatic hydrocarbons, chlorinated aliphatic and aromatic solvents, aliphatic alcohols, and aliphatic esters.

According to another and particularly interesting aspect of this invention, it has been found that the peroxides of this invention act as excellent vulcanizing agents for saturated elastomers, crosslinking agents for plastomers, and as initiators for radical polymerizations.

Vulcanization of the ethylene-propylene copolymer is carried out at a temperaure comprised between about 140° and 190°C, preferably between about 150° and 180°C, for periods of from about 5 to 200 minutes, preferably between about 5 and 15 minutes.

The concentration by weight of the peroxide should be between about 0.5% and 10%, preferably between about 2% and 5%, based on the elastomer.

A particularly suitable vulcanization recipe is the following:

| | |
|---|---|
| ethylene/propylene copolymer | 100 parts |
| carbon black | 20–80 parts |
| ZnO | 1 – 10 parts |
| sulfur | 0.15 – 0.5 parts |
| peroxide | 0.005 – 0.02 parts |

The use of the peroxides of the invention as crosslinking agents for plastomers finds specific application for polyolefins, particularly polyethylene, inasmuch as its mechanical resistance at high temperatures is improved, its brittleness at low temperatures is decreased, and its solubility in aliphatic hydrocarbons, aromatic hydrocarbons, and chlorinated hydrocarbons is decreased. Moreover, the resistance of the polymer to light, to weather and to aging is improved.

The crosslinking is carried out at a temperature comprised between about 100° and 200°C, preferably between about 145° and 165°C, at a pressure between about 50 – 200 kg/cm², for a period of time of from about 5 to 60 minutes, preferably from about 10 to 30 minutes.

The concentration by weight of the peroxide is between about 0.5 and 10%, preferably between about 2 and 5%, based on the plastomer.

The most significant advantages offered by the use of the peroxides according to this invention in the vulcanization of saturated elastomers and in the crosslinking of plastomers, are:

1. The capability of obtaining virtually odorless vulcanized and crosslinked products;
2. Absence of blooming phenomena;
3. Short vulcanization times and low vulcanization temperatures;
4. Improved effectiveness remains unchanged even in the presence of conventional additives such as fillers, reinforcing agents, additives, co-agents, plasticizers, pigments and anti-oxidants.

The following examples further illustrate the invention. All parts are by weight unless otherwise stated.

EXAMPLE 1

200 cc of ethyl ether, 60.6 g of 1.3-diisopropylbenzene-bis-hydroperoxide-sodium salt at 67%, 51 g of cyclopentanone at 99% and 20 g of ground anhydrous calcium chloride, were introduced into a flask provided with a stirrer.

This mixture was cooled down to from −15° −10°C and over a 20 minute period there were slowly introduced 60 g of HCl at 36%. The mixture was then stirred for 1 hour at −5°C. The ether solution was then washed with water and treated with anhydrous sodium sulfate.

The α-α′(1-hydroxy-cyclo pentylidene-1-peroxy)1,3 diisopropylbenzene thus obtained (53 g determined analytically) showed the following characteristics:

| | |
|---|---|
| Iodometric titre | 98% |
| Half life | 30 minutes at 98°C |
| Decomposition temperature | 45°C |
| C %: found 66.40 (calculated 66.98) | |
| H %: found 8.2 (calculated 8.69) | |

In a 10% toluene solution after 80 hrs. at 40°C no degradation occurred.

EXAMPLE 2

53 g of α-α′(1-hydroxy-cyclopentylidene-1-peroxy)1,3 diisopropylbenzene obtained according to Example 1 and dissolved in 200 cc of ethyl ether, 44 g of tert. butyl hydroperoxide at 80%, and 40 g of ground anhydrous calcium chloride, were introduced into a flask provided with a stirrer.

The ether solution was then cooled down to −10°C and over a 5 minute period there were introduced 20 g of hydrochloric acid at 36%. The temperature was permitted to rise to 0°C and the solution was stirred for 1 hour at 0°C.

The ether phase was then washed, first with water, then with NaOH at 5%, and then again with water. The solvent was then removed under vacuum at 30°C, thereby obtaining 69 g of product, namely, α-α′(1-tert.-butyl peroxy-cyclopentylidene-1-peroxy)1,3 diisopropylbenzene.

The product thus obtained showed the following characteristics:

| | |
|---|---|
| $d^{25} = 0.945$ | |
| $n_D^{25} = 1.447$ | |
| Iodometric titre: | 99% |
| Decomposition temperature: | 114°C |
| Half life at 123°C: | 30 minutes |
| C%: found 66.5 (calculated 66.88) | |
| H%: found 9.4 (calculated 9.36) | |

EXAMPLE 3

300 cc of ethyl ether, 41.8 g of 1,4-diisopropylbenzene bis-hydroperoxide at 97.3%, 37.8 g of 4-tert-butyl-cyclohexanone at 98%, and 18 g of ground anhydrous calcium chloride were introduced into a flask provided with a stirrer.

The mixture was then cooled down to 0°C and over a 5 minute period there were introduced 24 g of HCl at 36%. The temperature was maintained at 0°C and the mixture was kept under stirring for 1 hour.

The ether solution was then washed with water and then concentrated under vacuum, avoiding completely evaporation of the ether.

The α-α′(1-hydroxy-4-tert.-butyl-cyclohexylidene-1 peroxy)1,4-diisopropylbenzene thus obtained (66 g determined analytically) was kept in solution so as to be ready for subsequent reaction, and showed the following characteristics:

| | |
|---|---|
| Iodometric titre | 98.5% |
| Decomposition temperature | 62°C |
| Half-life at 112°C | 30 minutes |
| C %: found 70.4 (calculated 71.87) | |
| H %: found 10.1 (calculated 10.18) | |

EXAMPLE 4

150 g of ether solution containing 66 g of α-α'(1-hydroxy-4-tert.-butyl-cyclohexylidene-1-peroxy)1,4-diisopropylbenzene obtained according to Example 3, 44g of tert. butyl hydroperoxide at 80%, and 42 g of ground anhydrous calcium chloride were introduced into a flask provided with a stirrer.

The solution was then cooled down to −5°C and over a 5 minute period there were introduced 30 g of HCl at 36%. Care being taken not to exceed 0°C, the solution was then left under stirring at this temperature for 1 hour. The ether phase was washed with water, then with NaOH at 5%, and then again with water.

The solvent was subsequently removed under vacuum at 30°C, thereby obtaining a residue (76 g) identified as α-α'(1-tert.-butyl-peroxy-4-tert.-butyl-cyclohexylidene-1-peroxy) 1,4 diisopropylbenzene and having the following characteristics:

| | |
|---|---|
| Melting point | 32° – 34°C |
| Iodometric titre | 99.8% |
| Decomposition temperature | 109°C |
| Half life at 121°C | 30 minutes |
| C %: found 69.6 (calculated 70.75) | |
| H %: found 10.5 (calculated 10.40) | |

EXAMPLE 5

200 cc of benzene, 81 g of 1,3-diisopropylbenzene-bis-hydroperoxide-sodium salt at 67%, 33.5 g of cyclohexanone at 99%, and 25 g of ground anhydrous calcium chloride were introduced into a flask provided with a stirrer.

The mixture was then cooled down to −10°C and over a period of 30 minutes there were slowly introduced 80 g of HCl at 36%. The mixture was then left under stirring for 1 hour at −5°C.

The benzene solution was then washed with water and thereafter was dehydrated with anhydrous sodium sulfate.

The α-α'(1-hydroxy-cyclohexylidene-1-peroxy)1,3-diisopropylbenzene thus obtained (71 g determined analytically) was maintained in solution. This product showed the following characteristics:

| | |
|---|---|
| Iodometric titre: | 98% |
| Decomposition temperature: | 55°C |
| Half-life at 115°C | 30 minutes |
| C %: found 68.0 (calculated 68.22) | |
| H %: found 9.0 (calculated 9.07) | |

EXAMPLE 6

Into a flask fitted with a stirrer were introduced 71 g of α-α'(1-hydroxy-cyclohexylidene-1-peroxy)1,3-diisopropylbenzene dissolved in 200 cc of benzene (obtained according to Example 5), 58 g of tert.-butyl hydroperoxide at 80%, and 45 g of ground anhydrous calcium chloride.

The benzene solution was cooled down to 10°C and over a 5 minute period there were introduced 27 g of hydrochloric acid at 36%. The solution was then left under stirring for 1 hour at −5°/0°C. The organic phase was then washed, first with water, then with NaOH at 5%, and then again with water.

The benzene solution was then filtered on a layer of anhydrous sodium sulphate and celite and the solvent was removed under vacuum at 30°C.

Thereby were obtained 91 g of a product identified as α-α'(1-tert.-butyl-peroxy-cyclohexylidene-1 peroxy)1,3-diisopropylbenzene. The product showed the following characteristics:

| | |
|---|---|
| $d^{20} = 0.940$ | |
| $n_D^{25} = 1.452$ | |
| Iodometric titre: | 98.5% |
| Decomposition temperature: | 113°C |
| Half-life at 135°C | 31 minutes |
| C %: found 67.5 (calculated 67.81) | |
| H %: found 9.6 (calculated 9.6) | |

EXAMPLE 7

Into a flask provided with a stirrer were introduced 200 cc of benzene, 50 g of 1,3-diisopropylbenzene-bis-hydroperoxide (sodium salt) at 60%, 15.8 g of methyl-ethylketone, and 30 g of ground anhydrous calcium chloride. The mixture was cooled down to −5° to 0°C and over a 30 minute period there were then slowly introduced 49 g of HCl at 36%. The mixture was then stirred for 1 hour at 0°C. The benzene solution was washed with water and then dehydrated with anhydrous sodium sulfate.

The α-α'(2-hydroxy-n-butyliden-2 peroxy)1,3-diisopropylbenzene thus obtained (37 g determined analytically) showed the following characteristics:

| | |
|---|---|
| Iodometric titre: | 97% |
| Decomposition temperature: | 50°C |
| Half-life at 122°C | 30 minutes |
| C %: found 65.3 (calculated 64.84) | |
| H %: found 9.1 (calculated 9.25) | |

EXAMPLE 8

Into a flask provided with a stirrer were introduced 37 g of α-α'(2-hydroxy-n-butyliden-2-peroxy)1,3-diisopropylbenzene (obtained according to Example 7), dissolved in 200 cc of benzene, 40 g of tert.-butyl hydroperoxide at 75%, and 40 g of ground calcium chloride. The benzene solution was then cooled down to −5°C and over a 10 minute period there were introduced 30 g of hydrochloric acid at 36%. The temperature was allowed to rise to +5°C and the solution was stirred for 1 hour at this temperature. The benzene phase was then washed with water, then with NaOH at 5%, and again with water.

The solvent was then removed under vacuum at 30°C, thereby obtaining 39.5 g of a slightly straw-colored liquid residue identified as α-α'(2 tert.-butyl-peroxy-n-butyliden-2-peroxy) 1,3-diisopropylbenzene. This product showed the following characteristics:

```
d²⁵ = 0.915
n_D²⁵ = 1.437
Iodometric titre:                    94.6%
Decomposition Temperature:           105°C
Half-life at 114°C                   30 minutes
C %: found 65.8 (calculated 65.34)
H %: found 9.7 (calculated 9.79)
```

EXAMPLE 9

Into a flask provided with a stirrer were introduced 100 cc of benzene, 100 g of 1,3-diisopropylbenzene-bis-hydroperoxide (sodium salt) at 60%, 81 g of 2,6,8-trimethyl-4-nonanone and 30 g of ground anhydrous calcium chloride. The mixture was then cooled down to −5°C to 0°C, and over a 30 minute period there were intorduced 95 g of hydrochloric acid at 36%. The temperature rose to +5°C and the mixture was then left under stirring for 1 hour. The benzene phase was then washed with water and then treated with anhydrous sodium sulfate.

The α-α'(4-hydroxy-2,6,8 trimethyl-nonylidene-4-peroxy) 1,3-diisoprophylbenzene thus obtained (115 g determined analytically) showed the following characteristics:

```
Iodometric titre:                    94%
Decomposition temperature:           67°C
Half-life at 107°C                   30 minutes
C %: found 71.7 (calculated 72.68)
H %: found 10.9 (calculated 11.18)
```

EXAMPLE 10

115 g of α-α'(4-hydroxy-2,6,8-trimethyl-nonylidene-4 peroxy)1,3-diisopropylbenzene (obtained according to Example 9) dissolved in 100 cc of benzene, 79.5 g of tert. butyl hydroperoxide at 75%, and 40 g of ground anhydrous calcium chloride were introduced into a flask provided with a stirrer.

The solution was then cooled down to −5°C and over a 10 minute period there were introduced 40 g of hydrochloric acid at 36%. Due to the exotherm, the temperature rose to +5°C and the solution was then left under stirring at +5°C for 1 hour.

The benzene phase was washed with water, then with NaOH at 5%, and again with water. The solvent was then removed under vacuum at 30°C, thereby obtaining a liquid residue of a slight brownish color which was identified as α-α'(4-tert.-butyl-peroxy-2,6,8-trimethyl-nonylidene-4-peroxy)1,3-diisopropylbenzene, which product had the following characteristics:

```
n_D²⁵ = 1.4576
Iodometric titre:                    92%
Decomposition temperature:           109°C
Half-life at 116°C                   30 minutes
C %: found 71.3 (calculated 71.50)
H %: found 11.1 (calculated 11.18)
```

EXAMPLE 11

Into a flask provided with a stirrer there were introduced 300 cc of benzene, 65.4 g of 1,4-diisopropylbenzene-bis-hydroperoxide at 95%, 50 g of cyclododecanone, and 50 g of ground anhydrous calcium chloride. The mixture was then cooled down to −10°C and over a 25 minute period there were introduced 60 g of hydrochloric acid at 36%. The mixture was stirred for 1 hour at +5°C. The benzene solution was then washed with water and thereafter was dehydrated with anhydrous sodium sulfate.

The α-α'(1-hydroxy-cyclododecylidene-1 peroxy)1,4-diisopropylbenzene thus obtained (80 g determined analytically) showed the following characteristics:

```
Iodometric titre:                    98%
Decomposition temperature:           59°C
Half-life at 114°C:                  30 minutes
C %: found 73.3 (calculated 73.17)
H %: found 10.3 (calculated 10.58)
```

EXAMPLE 12

Into a flask provided with a stirrer were introduced 80 g of α-α'(1-hydroxy-cyclododecylidene-1 peroxy) 1,4-diisopropylbenzene (obtained according to Example 11) dissolved in 300 cc of benzene, 66.7 g of tert.-butyl-hydroperoxide at 66.7%, and 40 g of ground anhydrous calcium chloride. The benzene solution was then cooled down to 0°C and over a 10 minute period there were introduced 5 g of hydrochloric acid at 36%.

The temperature was then allowed to rise to +5°C and the solution was then stirred for 1 hour at this temperature (+5°C). The benzene phase was then washed with water, with NaOH at 5%, and then again with water.

The solvent was then removed under vacuum at 40°C, thereby obtaining 48 g of a yellow liquid residue identified as α-α'(1-tert.-butyl-peroxy-cyclododecylidene-1 peroxy) 1,4-diisopropylbenzene. The product showed the following characteristics:

```
n_D²⁵ = 1.4580
Iodometric titre:                    99 %
Decomposition temperature:           109°C
Half-life at 120°C:                  30 minutes
C %: found 0.2 (calculated 71.89)
H %: found 10.9 (calculated 10.7)
```

EXAMPLE 13

Into a flask provided with a stirrer, were introduced 50 cc of benzene, 50 cc of ethyl ether, 60.6 g of 1.3diiso-propyl-benzene-bis-hydroperoxide (sodium salt) at 67%, 27.7 g of benzyl-methyl-ketone at 97%, and 30 g of ground anhydrous calcium chloride. This mixture was then cooled down to −15°C and then were slowly added, over a 30 minute period, 60 g of HCl at 36%. Thereafter the mixture was kept under stirring for 1 hour at −5°C.

The organic solution thus obtained was then washed with water and then was dehydrated with anhydrous sodium sulfate. The product thus obtained (37 g determined analytically), identified as alpha-alpha'[2-hydroxy-(3-phenyl) propylidene-2 peroxy] 1,3-diisopropylbenzene, was kept in solution.

An isolated analytical sample showed the following characteristics:

```
Iodometric titration:                93.5%
```

-continued

| | |
|---|---|
| Decomposition temperature: | 70°C |
| Half-life at 104°C: | 30 minutes |
| C %: found 71.9% (calculated 72.85) | |
| H %: found 7.4% (calculated 7.74) | |

EXAMPLE 14

Into a flask provided with a stirrer were introduced 37 g of α-α'[2-hydroxy-(3-phenyl)propylidene-2 peroxy]1,3 diisopropylbenzene (obtained according to Example 13) dissolved in 50 cc of benzene and 50 cc of ether, 45.2 g of tert.-butyl hydroperoxide at 80%, and 20 g ground anhydrous calcium chloride. This solution was then cooled down to −5°C and in over a 10 minute period there were added 20 g of hydrochloric acid at 36%.

The exotherm caused the temperature to rise to +5°C and the solution was maintained at this temperature for 1 hour under stirring. Thereafter the organic phase was washed with water, with NaOH at 5%, and again with water until neutrality.

Then the solvent was removed under vacuum at 50°C, thereby obtaining a slightly opalescent liquid residue (44 g), identified as α-α'[2-tert.-butyl-peroxy-(3-phenyl)propylidene-2 peroxy]1,3-diisopropylbenzene, having the following characteristics:

| | |
|---|---|
| $n_D^{20} = 1.4988$ | |
| Iodometric titration: | 75% |
| Decomposition temperature: | 132°C |
| Half-life at 123°C: | 30 minutes |
| C %: found 72.9% (calculated 71.44) | |
| H %: found 8.5% (calculated 8.52) | |

EXAMPLE 15

Into a flask provided with a stirrer were introduced 50 cc of benzene, 50 cc of ethyl ether, 21.4 g of 1,3-diisopropylbenzene-bis-hydroperoxide (sodium salt) at 67%, 19.3 g of 4-tert.-butyl-cyclohexanone and 10 g of ground anhydrous calcium chloride. This mixture was then cooled down and over a 20 minute period there were introduced dropwise 20 g of HCl at 36%. The mixture was then subjected to stirring for 1 hour at −5°C.

The organic solution was washed with water and was then dehydrated with anhydrous sodium sulfate. The residue (32 g determined by analysis), identified as α-α'[1-hydroxy-(4-tert.-butyl)-cyclohexylidene-1 peroxy]1,3-diisopropylbenzene, was kept in a solution. An analytical isolated sample showed the following characteristics:

| | |
|---|---|
| Iodometric titre: | 95% |
| Decomposition temperature: | 78°C |
| Half-life at 110°C | 30 minutes |
| C %: found 71.3% (calculated 71.87) | |
| H %: found 10.0% (calculated 10.18) | |

EXAMPLE 16

Into a flask provided with a stirrer were introduced 32 g of α-α'[1-hydroxy-(4-tert.-butyl)cyclohexylidene-1 peroxy]1,3-diisopropylbenzene, dissolved in 50 cc of benzene and 50 cc of ether, and 15 g of anhydrous calcium chloride. Over a period of 20 minutes there were then introduced into the mixture, at a temperature of −15°C, 43.9 g of cumene hydroperoxide at 83.4%. The solution was cooled down again to −15°C, and there were introduced 10 g of HCl at 36% over a 10 minute period. The exotherm caused the temperature to rise to −5°C and the solution was then left under stirring for 1 hour at between −5° and 0°C.

The organic phase was washed with water, with NaOH at 5%, and then again with water until reaching neutrality. The solvent was then removed under vacuum at 50°C, thereby obtaining a slightly oily residue, identified as an α-α'[1 cumyl-peroxy(tert.-butyl)cyclohexylidene-1 peroxy]1,3-diisopropylbenzene, and it showed the following characteristics:

| | |
|---|---|
| $n_D^{20} = 1.4985$ | |
| Iodometric titre: | 90% |
| Decomposition temperature: | 114°C |
| Half-life at 125°C: | 30 minutes |
| C %: found 75.1% (calculated 74.4) | |
| H %: found 8.5% (calculated 8.52) | |

EXAMPLE 17

200 cc of n-hexane, 50 g of 1,3-diisopropylbenzene-bis-hydroperoxide-sodium salt at 60%, 29 g of acetoacetic acid ethyl ester at 99% and 30 g of ground anhydrous calcium chloride were introduced into a flask provided with a stirrer. The mixture was then cooled down to −10°–5°C and over a period of 30 minutes there were introduced 45 g of HCl at 36%. The mixture was then left under stirring for 1 hour at −5°C. The organic phase was then washed with water and thereafter was dehydrated with anhydrous sodium sulfate. The α-α'[2-hydroxy-(3 ethoxy-carbonyl)-isopropylidene-2 peroxy]1,3-diisopropylbenzene thus obtained (43 g determined analytically) showed the following characteristics:

| | |
|---|---|
| Iodometric titre | 95 % |
| Decomposition temperature | 47°C |
| Half-life at 118°C | 30 minutes |
| C %: found 60.1 (calculated 59.24) | |
| H %: found 7.65 (calculated 7.87) | |

EXAMPLE 18

Into a flask fitted with a stirrer were introduced 43 g of α-α'[2-hydroxy-(3 ethoxy-carbonyl)-isopropylidene-2 peroxy]1,3-diisopropylbenzene (obtained according to example 17) dissolved in 200 cc of n-hexane, 40 g of tert.-butyl hydroperoxide at 75 % and 40 g of ground anhydrous calcium chloride. The solution was cooled down to −10°C and over a 10 minute period there were introduced 30 g of HCl at 36 %. The temperature was allowed to rise to 0°C, and the solution was stirred for 1 hour at this temperature. The organic phase was then washed with water, then with NaOH at 5 % and then again with water. The solvent was removed under vacuum care being taken not to exceed 30°C, thereby obtaining 47 g of slightly yellow-coloured viscous residue identified as α-α'[2-tert.-butyl-peroxy(3 ethoxy-carbonyl) isopropylidene-2 peroxy]1,3-diisopropylbenzene. This product showed the following characteristics:

| | |
|---|---|
| $d^{25}$ | = 0.937 |
| $n_D^{25}$ | = 1.489 |
| Iodometric titre | = 97 % |
| Decomposition temperature | = 109°C |
| Half-life at 118°C | = 30 minutes |
| C %: found 61.4 (calculated 60.93) | |
| H %: found 8.63 (calculated 8.63) | |

EXAMPLE 19

Into a flask provided with a stirrer were introduced 150 cc of benzene, 23.5 g of 1,4 diisopropylbenzene-bis-hydroperoxide at 97.3 %, 18 g of acetoacetic acid ethylester at 99 % and 10 g of anhydrous calcium chloride. The mixture was then cooled down to −10°C and over a 5 minute period there were introduced 12 g of HCl at 36 %. The mixture was then stirred at this temperature for 1 hour. The benzene phase was washed with water and then treated with anhydrous sodium sulfate. The α-α'[2-hydroxy-(3-ethoxycarbonyl) isopropylidene-2 peroxy]1,4 diisopropylbenzene thus obtained (29 g analitically determined) showed the following characteristics:

| | |
|---|---|
| Iodometric titre | 97 % |
| Decomposition temperature | 45°C |
| Half-life at 115°C | 30 minutes |
| C %: found 58.6 (calculated 59.24) | |
| H %: found 7.43 (calculated 7.87) | |

EXAMPLE 20

150 cc of benzene containing 29 g of α-α'[2-hydroxy(3-ethoxycarbonyl) isopropylidene-2-peroxy]-1,4 diisopropyl-benzene (obtained according to example 19) and 15 g of anhydrous calcium chloride were introduced into a flask fitted with a stirrer. Over a 20 minute period to −15°C there were introduced 43.9 g of tert.-cumyl hydroperoxide at 83,4 %. The temperature was maintained to −15°C and over a 10 minute period there were introduced 10 g of HCl at 36 %. Due to the exotherm the temperature rose to −5°C and at this temperature the solution was then left under stirring for 1 hour. The organic phase was then washed with water, then with NaOH at 5% and again with water until neutrality. The solvent was removed under vacuum at 30°C thereby obtaining 38 g of a slightly oily straw-colored residue identified as α-α'[2-cumyl-peroxy (3-ethoxy carbonyl) isopropylidene-2 peroxy]1,4 diisopropylbenzene having the following characteristics:

| | |
|---|---|
| $n_D^{20}$ | = 1.521 |
| Iodometric titre | = 93 % |
| Decomposition temperature | = 121°C |
| Half-life at 122°C | = 30 minutes |
| C %: found 65.3 (calculated 66.82) | |
| H %: found 7.32 (calculated 7.74) | |

EXAMPLE 21

VULCANIZATION:

Vulcanization tests were carried out on mixes of an ethylene-propylene copolymer having a molar ratio ethylene/propylene 50/50 and a viscosity Mooney ML (1 + 4) 100°C = 35 In Table 1 there were compared the vulcanization rates determined on the same mixes, containing as peroxides, respectively:

α-α'(1-tert.-butyl-peroxy-cyclopentylidene-1-peroxy) 1,3-diisopropylbenzene;

α-α'(1-tert.-butyl-peroxy-4-tert.-butyl-cyclohexylidene-1-peroxy) 1,4-diisopropylbenzene;

α-α'(1-tert.-butyl-peroxy-cyclohexylidene-1-peroxy) 1,3 diisopropylbenzene;

α-α'[2-ter.-butyl peroxy (3-ethoxycarbonyl) isopropylidene-2 peroxy]1,3 diisopropylbenzene; dicumylperoxide.

The vulcanization rate was determined at 177°C on a Monsanto TM-10 rheometer. The mixes used in the test were of the following composition:

| | |
|---|---|
| ethylene-propylene copolymer | 100 parts |
| carbon black | 50 parts |
| ZnO | 3 parts |
| sulfur | 0.32 parts |
| peroxide | 0.01 mol |

Table 2 reports the physical characteristics of vulcanized products obtained by using as peroxides, respectively:

α-α'(1-tert.-butyl-peroxy-cyclopentylidene-1-peroxy) 1,3-diisopropylbenzene;

α-α'(1-tert.-butyl-peroxy-4-tert.-butyl-cyclohexylidene-1-peroxy)1,4-diisopropylbenzene;

α-α'(1-tert.-butyl-peroxy-cyclohexilidene-1-peroxy) 1,3-diispropylbenzene;

for vulcanization times comprised between 5 and 60 minutes at 150°C, in comparison with the physical properties of the vulcanized products obtained by using dicumyl peroxide and operating at 165°C for a vulcanization time of 30 minutes (these being the optimal conditions for said peroxide). From the results reported in Table 2, it is quite evident that at low temperatures high vulcanization rates and better physical characteristics of the vulcanized product are obtained with the peroxides of the invention as contrasted to the use of dicumyl peroxide.

TABLE 1

Vulcanization Rate

| Peroxide | | | Vulvanization at the RHEOMETER | |
|---|---|---|---|---|
| TYPE | Parts per 100 g of ethylene/propylene copolymer | | Vulcanization temperature °C | Vulcanization time minutes |
| | g | moles | | |
| 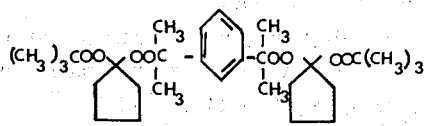 | 5,38 | 0,01 | 177 | 5 |
| 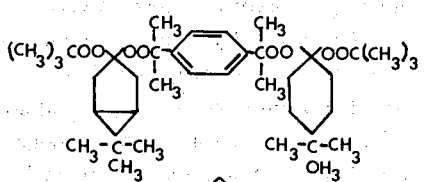 | 6,79 | " | " | 4,5 |
| 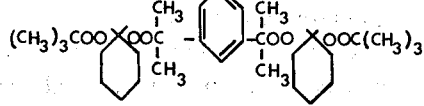 | 5,66 | " | " | 6 |
| α-α'[2-ter.-butylperoxy(3-ethoxycarbonyl)isopropylidene-2-peroxy]1,3 diisopropylbenzen | 6,3 | " | " | 7 |
| Dicumylperoxide | 2,70 | " | " | 14 |

TABLE 2

Physical Characteristics of the Vulcanized Product

| Peroxide | Parts per 100 g of ethylene/propylene copolymer | | Vulcanization | |
|---|---|---|---|---|
| | moles | g | Temperat. °C | Time minute |
| 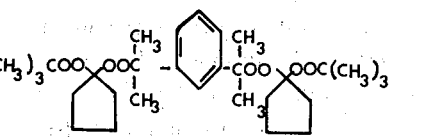 | 0,01 | 5,38 | 150<br>"<br>"<br>"<br>" | 5<br>10<br>15<br>30<br>60 |
| 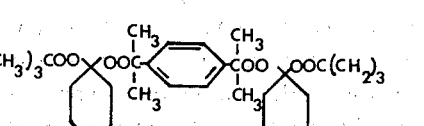 | 0,01 | 6,79 | 150<br>"<br>"<br>"<br>" | 5<br>10<br>15<br>30<br>60 |
| 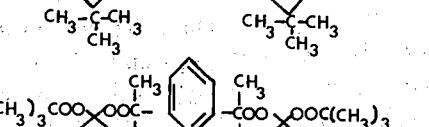 | 0,01 | 5,66 | 150<br>"<br>"<br>"<br>" | 5<br>10<br>15<br>30<br>60 |
| 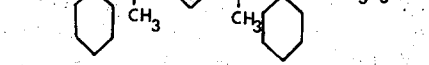 | 0,01 | 2,70 | 165 | 30 |

TABLE 2-continued

Physical properties of the vulcanized product

| Tensile strength kg/cm² | Elongation at break, % | Modulus at 100% kg/cm² | Modulus at 200% kg/cm² | Modulus at 300% kg/cm² | I.R.H.D. hardness |
|---|---|---|---|---|---|
| 192 | 510 | 23 | 50 | 91 | 65–66 |
| 198 | 470 | 25 | 55 | 108 | 66 |
| 187 | 410 | 22 | 54 | 104 | 67 |
| 198 | 420 | 23 | 61 | 119 | 67 |
| 186 | 380 | 25 | 68 | 130 | 67 |
| 201 | 350 | 25 | 78 | 155 | 68–69 |
| 203 | 340 | 27 | 81 | 164 | 69 |
| 202 | 350 | 26 | 75 | 158 | 69 |
| 190 | 330 | 28 | 84 | 168 | 69 |
| 178 | 340 | 25 | 72 | 148 | 69 |
| 199 | 490 | 22 | 54 | 103 | 66 |
| 195 | 460 | 23 | 53 | 104 | 67 |
| 203 | 440 | 24 | 56 | 110 | 67–68 |
| 202 | 410 | 25 | 63 | 126 | 68 |
| 188 | 400 | 24 | 57 | 123 | 68 |
| 180 | 410 | 21 | 58 | 119 | 68 |

EXAMPLE 22

On a mix having the following composition:

| | |
|---|---|
| ethylene/propylene copolymer | 100 parts |
| carbon black | 50 parts |
| ZnO | 3 parts |
| sulfur | 0,32 parts |
| α-α'[2-tert.-butyl peroxy (3-ethoxycarbonyl) isopropylidene-2 peroxy]1,3 diisopropylbenzene | 0,01 mol | was carried out the vulcanization test at 150°C for 15 minutes. The vulcanized product showed the following physical characteristics:

| | |
|---|---|
| Tensile strength (kg/cm²) | 185 |
| Elongation at break (%) | 412 |
| Modulus at 200% (kg/cm²) | 61 |
| Modulus at 300% (kg/cm²) | 108 |
| I.R.H.D. hardness | 67–68 |

EXAMPLE 23

CROSSLINKING

The crosslinking tests were carried out on mixes substantially consisting of low-density polyethylene and peroxide.

In Table 3 there are recorded the physical characteristics of polyethylene crosslinked using the peroxides according to the invention, that is, α-α'(1-tert.-butyl-peroxy-cyclopentyliden-1-peroxy) 1,3-diisopropylbenzene, α-α'(1-tert.-butyl-peroxy-4-tert.-butyl-cyclohexylidene-1-peroxy) 1,4 diisopropylbenzene, and the known peroxide (dicumylperoxide).

EXAMPLE 24

The determination of the degree of swelling was carried out on the crosslinked product. By "degree of swelling" is meant the volume of solvent absorbed by unit of volume of crosslinked polyethylene.

The method consists in suspending a small basket or cage containing a crosslinked polyethylene plate of about 0.2 g in a test tube containing 100 cc of xylene stabilized with 0.1 g of the phenolic antioxidant 4,4-thio-bis (3-methyl-6tert.-butyl-phenol). The test is carried out for 21 hours at 80°C. The degree of swelling (S) is determined from the following formula:

$$S = 1.07 \cdot \frac{(a-b) - c}{c} + 1$$

wherein:

a = weight of the test sample after 21 hours at 80°C in xylene,
b = weight of the test sample before the test,
c = weight of the test sample after drying at the end of the test.

$$1.07 = \frac{\text{density of polyethylene at 80°C}}{\text{density of xylene at 80°C}}$$

The obtained results, compared with those in which dicumyl-peroxide was used, are listed in Table 4.

TABLE 3

Crosslinking of low-density (0.918) polyethylene
Physical characteristics.

| PEROXIDE | Moles of peroxide in 100g of polyethylene | Crosslinking Time minutes | Crosslinking Temper. °C | Yield point kg/cm² | Tensile strength Kg/cm² | Elongation at break % |
|---|---|---|---|---|---|---|
| None | — | 20 | 145 | 57,8 | 73 | 150 |
| (CH₃)₃COO—[cyclopentyl(CH₃)]—OOC—C₆H₄—COO—[cyclopentyl(CH₃)]—OOC(CH₃)₃ | 0,01 | 20 | 145 | 55 | 150 | 570 |

TABLE 3-continued

Crosslinking of low-density (0.918) polyethylene
Physical characteristics.

| PEROXIDE | Moles of peroxide in 100g of poly- ethylene | Crosslinking | | Yield point kg/cm² | Tensile strength Kg/cm² | Elonga- tion at break % |
|---|---|---|---|---|---|---|
| | | Time min- utes | Temper. °C | | | |
| 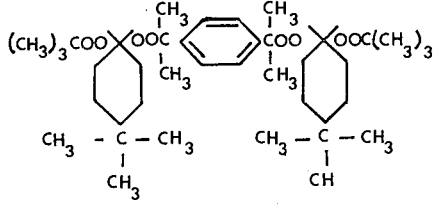 | 0,01 | 20 | 145 | 52,7 | 137 | 260 |
| Dicumylperoxide | 0,01 | 20 | 145 | 52,9 | 132 | 456 |

TABLE 4

Crosslinking of low-density (0.918) polyethylene
Degree of swelling.

| PEROXIDE | Moles of peroxide in 100g of poly- ethylene | Crosslinking | | Degree of swelling |
|---|---|---|---|---|
| | | Time minutes | Temper. °C | |
| 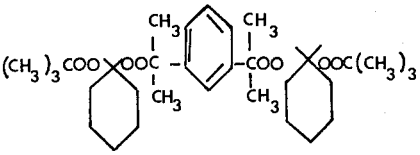 | 0,01 | 20 | 145 | 16,5 |
| | 0,01 | 20 | 145 | 20,2 |
| Dicumylperoxide | 0,01 | 20 | 145 | 21,3 |

Variations can, of course, be made without departing from the spirit and scope of the invention.

Having thus described our invention, what we desire to secure by Letters Patent and hereby claim is:

1. A peroxide of the formula:

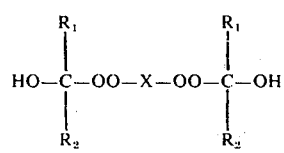

wherein each $R_1$ is alkyl having 1–5 carbon atoms; each $R_2$ is alkylene alkoxy carbonyl, wherein each alkylene and alkoxy have 1–4 carbon atoms; and X is phenylene or phenylenedialkylene.

2. An organic peroxide as defined in claim 1 and being selected from the group consisting of α-α′[2-hydroxy-(3-ethoxycarbonyl)-isopropylidene-2-peroxy] 1,3 diisopropylbenzene and α-α′[2-hydroxy-(3-ethoxycarbonyl)-isopropylidene-2-peroxy] 1,4 diisopropyl-benzene.

3. A peroxide according to claim 1 which is α,α′-[2-hydroxy-3-ethoxycarbonyl-isopropylidene-2-peroxy]1,3-diisopropyl-benzene.

4. A process for the preparation of a peroxide as defined in claim 1, this process comprising reacting a carbonyl compound of the formula:

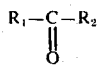

in the presence of an acid catalyst selected from the group consisting of HCl, $H_2SO_4$ and $HClO_4$ and a dehydrating agent selected from the group consisting of calcium chloride and sodium sulfate, with a bis-hydroperoxide of the formula:

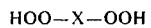

wherein $R_1$, $R_2$ and X are as defined in claim 1, at a temperature of from about −30° to +80°C.

5. The process of claim 4 wherein said reaction is carried out at from about −10° to +50°C.

6. The process of claim 4 wherein the molar ratio of bis-hydroperoxide to carbonyl compound is from about 1:1.2 to 1:10.

7. The process of claim 6 wherein said molar ratio is from about 1:1.5 to 1:5.

8. The process of claim 4, wherein a solvent is employed, said solvent being selected from the group consisting of diethyl ether, benzene and mixtures thereof.

* * * * *

PO-1050
(5/69)

UNITED STATES PATENT OFFICE
CERTIFICATE OF CORRECTION  Sheet 1 of 4

Patent No. 3,980,712                    Dated September 14, 1976

Inventor(s) Egeo SACRINI and Claudio CAVALLOTTI

It is certified that error appears in the above-identified patent and that said Letters Patent are hereby corrected as shown below:

Title page, under "Related U.S. Application Data": "Aug. 8, 1970," should read -- Aug. 7, 1970, --; the formula in the Abstract:

" 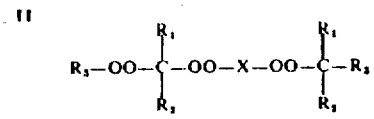 " should read -- 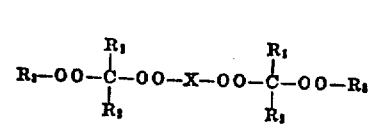 --;

line 7 after the formula: "monohydroxide" should read -- monohydroperoxide --.

Column 1, line 5: "Aug. 8, 1970" should read -- Aug. 7, 1970 --.

Column 2, line 31: "monohydroxide of the tertiary type" should read -- tertiary monohydroperoxide --; line 42: "alcoxy" should read -- alkoxy --.

Column 3, line 43: "2,5-dimethyl-2,5-dihydroperoxide-hexene-3;" should read -- 2,5-dimethyl-2,5-dihydroperoxide-hexane-3; --; line 48: "ethyl-acetacetate" should read -- ethyl-acetocetate --; lines 49-50: "ccyclododecanone" should read -- cyclododecanone --.

Column 9, line 17: "intorduced" should read -- introduced --; line 24: "1,3-diisoprophylbenzene" should read -- 1,3-diisopropylbenzene --.

Column 10, line 44: "0.2 (calculated" should read -- 70.2 (calculated --.

UNITED STATES PATENT OFFICE
CERTIFICATE OF CORRECTION

Patent No. 3,980,712  Dated September 14, 1976

Inventor(s) Egeo SACRINI and Claudio CAVALLOTTI

It is certified that error appears in the above-identified patent and that said Letters Patent are hereby corrected as shown below:

Column 11, line 31: "1,4988" should read -- 1.4988 --.

Column 12, line 17: "1,4985" should read -- 1.4985 --.

Column 13, lines 3 and 4:  " = 0,937" should -- = 0.937 --;
                             = 1,489    read       1.489
line 29: "analitically" should read -- analytically --;
line 50: "83,4%" should read -- 83.4% --; line 66: "1,521" should read 1.521 --.

Column 14, lines 6 and 7:
"found 65,3 " should   -- found 65.3 --;
 found 7,32    read       found 7.32
line 17: "100°C = 35 In" should read -- 100°C = 35. In --

Columns 15-16, Table 1, second formula:

"  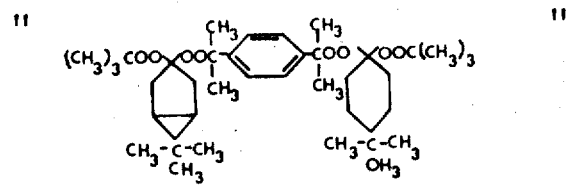  "

should read     --   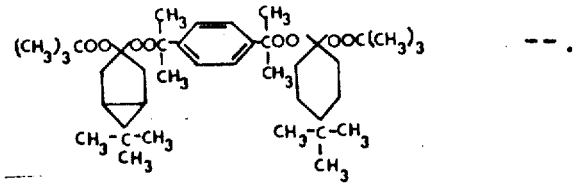   --.

UNITED STATES PATENT OFFICE
CERTIFICATE OF CORRECTION

Patent No. 3,980,712　　　　　　　Dated September 14, 1976

Inventor(s) Egeo SACRINI and Claudio CAVALLOTTI

It is certified that error appears in the above-identified patent and that said Letters Patent are hereby corrected as shown below:

Columns 15-16, Table 1, lines 2 and 3 after third formula: "1,3-diisopropylbenzen" should read -- 1,3-diisopropylbenzene --; Table 1, columns 2 and 3:

| "5,38 | 0,01 " | should read | -- 5.38 | 0.01 --; |
|---|---|---|---|---|
| 6,79 | " |  | 6.79 | " |
| 5,66 | " |  | 5.66 | " |
| 6,3 | " |  | 6.3 | " |
| 2,70 | " |  | 2.70 | " |

Table 1, last column: "4,5" should read -- 4.5 --.

Columns 15-16, Table 2, second formula:

" 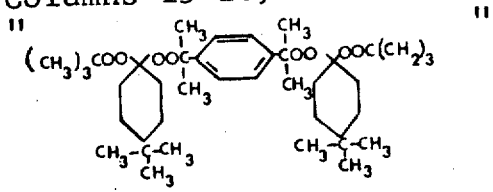 "

should read -- 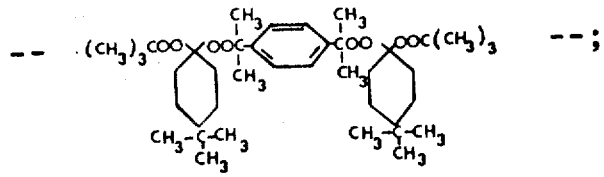 --;

Table 2, After third formula: should read -- Dicumylperoxide --; Table 2, columns 2 and 3:

| "0,01 | 5,38" | should read | -- 0.01 | 5.38 --. |
|---|---|---|---|---|
| 0,01 | 6,79 |  | 0.01 | 6.79 |
| 0,01 | 5,66 |  | 0.01 | 5.66 |
| 0,01 | 2,70 |  | 0.01 | 2.70 |

UNITED STATES PATENT OFFICE
CERTIFICATE OF CORRECTION

Patent No. 3,980,712  Dated September 14, 1976

Inventor(s) Egeo SACRINI and Claudio CAVALLOTTI

It is certified that error appears in the above-identified patent and that said Letters Patent are hereby corrected as shown below:

Column 17, lines 29 and 31:
"0,32 parts"    should read    -- 0.32 parts --.
0,01 mol                       0.01 mol Columns 17-18, Table 3, columns 2 and 5:
"       57,8"   should read --              57.8 --.
 0,01                          0.01

Columns 19-20, Table 3, columns 2 and 5:
"0,01    52,7"  should read    -- 0.01      52.7 --.
 0,01    52,9                     0.01      52.9

Table 4, columns 2 and 5:
"0,01    16,5"  should read    -- 0.01      16.5 --.
 0,01    20,2                     0.01      20.2
 0,01    21,3                     0.01      21.3

Signed and Sealed this

Eighth Day of February 1977

[SEAL]

Attest:

RUTH C. MASON
Attesting Officer

C. MARSHALL DANN
Commissioner of Patents and Trademarks